United States Patent
Bungo

(10) Patent No.: US 8,281,639 B2
(45) Date of Patent: Oct. 9, 2012

(54) METHOD FOR ADJUSTING THE DETECTOR OF A CHROMATOGRAPH

(75) Inventor: Hajime Bungo, Muko (JP)

(73) Assignee: Shimadzu Corporation, Kyoto (JP)

(*) Notice: Subject to any disclaimer, the term of this patent is extended or adjusted under 35 U.S.C. 154(b) by 507 days.

(21) Appl. No.: 12/614,730

(22) Filed: Nov. 9, 2009

(65) Prior Publication Data

US 2010/0116016 A1    May 13, 2010

(30) Foreign Application Priority Data

Nov. 12, 2008    (JP) .................. 2008-289817

(51) Int. Cl.
    G01N 21/00    (2006.01)
(52) U.S. Cl. ........................................ 73/1.02
(58) Field of Classification Search .......... 73/1.02; 702/89, 176; 713/400
    See application file for complete search history.

(56) References Cited

U.S. PATENT DOCUMENTS

| 2005/0119846 A1* | 6/2005 | Mori ............... 702/89 |
| 2007/0143641 A1* | 6/2007 | Rhodes ............. 713/400 |

FOREIGN PATENT DOCUMENTS

| CN | 1409108 A | 4/2003 |
| JP | 6-174709 A | 6/1994 |
| JP | 09-203724 A | 8/1997 |
| JP | 2006-286210 A | 10/2006 |
| JP | 2006-292579 A | 10/2006 |
| JP | 2007-292662 A | 11/2007 |
| JP | 2008-180612 A | 8/2008 |

OTHER PUBLICATIONS

Chinese Office Action dated Apr. 26, 2012, issued in corresponding Chinese Patent Application No. 200910206421.9.
Japanese Office Action dated Jun. 5, 2012, issued in corresponding Japanese Patent Application No. 2008-289817.

* cited by examiner

Primary Examiner — Hezron E Williams
Assistant Examiner — Nathaniel Kolb
(74) Attorney, Agent, or Firm — Sughrue Mion, PLLC

(57) ABSTRACT

The present invention provides a detector for a chromatograph capable of obtaining the accurate retention time, even if there is a frequency deviation of the clock signal for determining the timing of data sampling, by conforming the progress of the detector internal time accompanied with the repetition of the sampling to that of real time. In the detector, consecutive data sampling intervals are defined to be a time adjustment period, and in one time adjustment period, each of the sampling intervals whose number is given as the interpolation value M is elongated by a predetermined number of clock counts compared to each of the other sampling intervals. If the clock signal has a positive frequency deviation, the apparatus internal time determined by the clock signal progresses faster than real time. However, providing the interpolation value M corresponding to the amount of the frequency deviation elongates the time adjustment period on the basis of the apparatus internal time, to be conformed to the time adjustment period on the basis of real time which is determined by the sampling period.

4 Claims, 4 Drawing Sheets

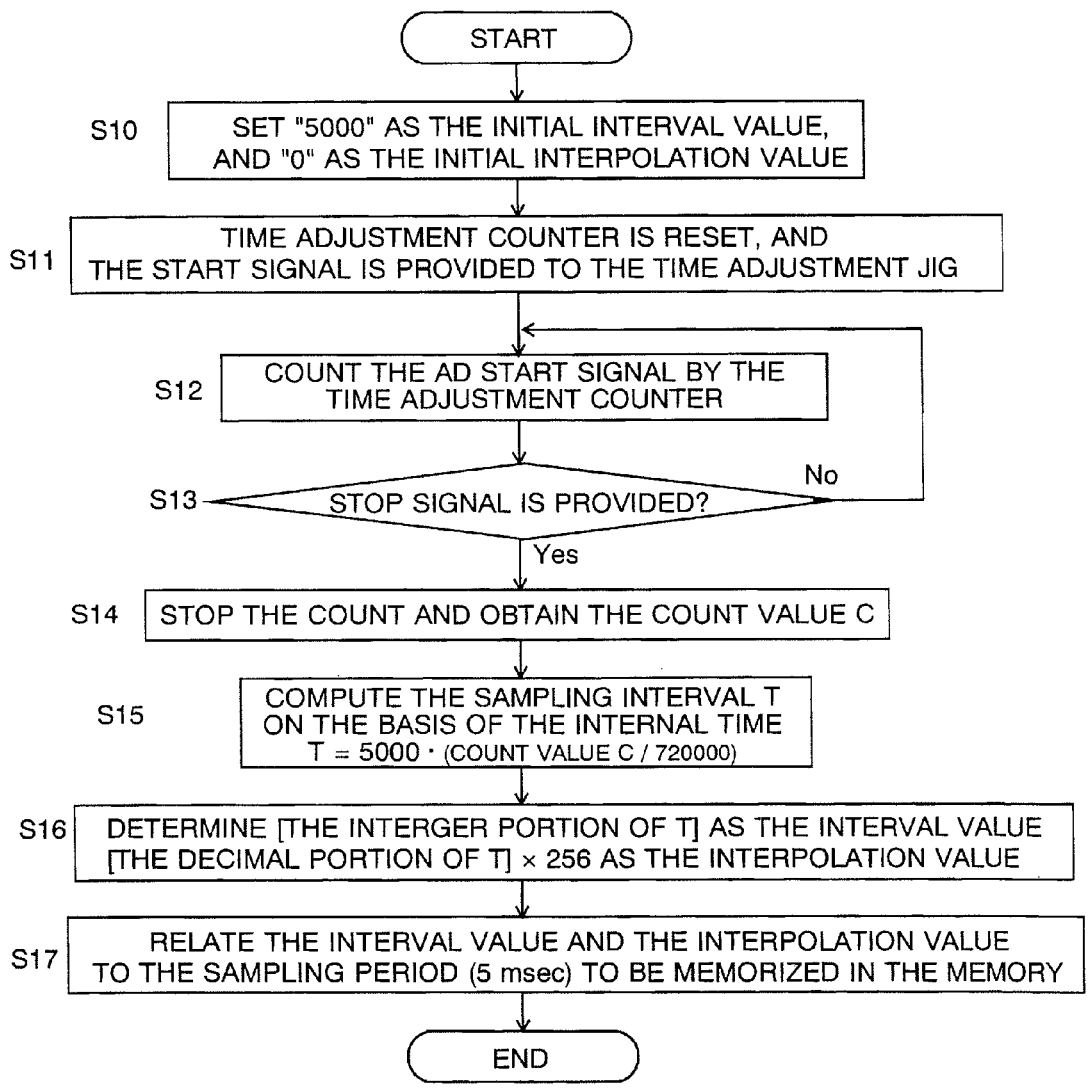

NO TIME ADJUSTMENT (CONVENTIONAL TECHNIQUE)

WITH A TIME ADJUSTMENT (PRESENT INVENTION)

METHOD FOR ADJUSTING THE DETECTOR OF A CHROMATOGRAPH

The present invention relates to a detector for a chromatograph such as a liquid chromatograph (LC) and gas chromatograph (GC). More precisely, it relates to a detector for a chromatograph incorporating an A/D converter for sampling an analog detection signal at predetermined data sampling intervals to convert it to digital values. It also relates to a method for adjusting such a detector.

BACKGROUND OF THE INVENTION

In a liquid chromatograph (LC), a variety of detectors, such as an absorbance detector, fluorescence detector, deferential refractive index detector, and electric conductivity detector, are used. Such detectors have an analog-to-digital (A/D) converter for sampling an analog detection signal at predetermined data sampling intervals and converting the sampled analog values into digital values, and send the digitized detection signal to a personal computer or other devices to perform a data processing task (refer to Patent Document 1 and other documents). The sampling period in the A/D converter is usually determined in view of the following factors: a short sampling period in the A/D converter increases the temporal resolution; however, it also increases the amount of data generated per unit time, increasing the required amount of memory as well as the load on the communication system and the central processing unit (CPU). On the other hand, a long sampling period decreases the temporal resolution and steep peaks cannot be reproducibly detected, although it decreases the load on the communication system and CPU. Considering such advantages and disadvantages, the sampling period is set to be an appropriate value or range, e.g. approximately 1 through 100 [msec].

Generally, the signal for determining the timing of the data sampling in the A/D converter is generated by counting a radio-frequency reference clock signal created using a crystal oscillator. Hence, the frequency deviation of the crystal oscillator mainly causes the lag between the progress of real time (which is based on the International Atomic Time) and that of the time inside the detector (which will be hereinafter called an "apparatus internal time") which accompanies the repetition of the data sampling. Since the retention time of a peak on the chromatogram generated based on the detection signal is based on the apparatus internal time, the lag between the apparatus internal time and real time appears as a lag of the retention time on the chromatograph.

The maximum frequency deviation of generally available crystal oscillators is approximately ±100 through 200 [ppm]. If the frequency is deviated to a higher value, the apparatus internal time progresses faster than real time. Therefore, the retention time of a peak on a chromatograph becomes longer than it really is in accordance with the amount of the lag. For example, assuming that the frequency deviation of a crystal oscillator is +150 [ppm], the time lag after 100 minutes from the initiation of an analysis is 0.015 minutes, which is practically negligible. However, after 2000 minutes from the initiation of the analysis, the time lag increases to 0.3 minutes. This lag can be easily recognized on the chromatogram by a user, and is not negligible.

In the case where an eluate whose components are separated in a column is bifurcated and the bifurcated eluates are respectively and simultaneously detected by two detectors, each of the detectors has its own A/D converter which samples data in accordance with a different reference clock signal. Therefore, the difference of the frequency deviations of the two reference clock signals, i.e. those of the crystal oscillators for generating a reference clock signal, emerges as the difference of the retention times on the chromatogram obtained in each detector.

FIG. 6A illustrates an example of an output screen (only a chromatogram display screen) shown after a predetermined time has passed from the initiation of an analysis in a conventional LC system. In this example, the chromatogram data and other data were initiated to be plotted at the time when 2000 minutes had elapsed from the initiation of the analysis, and FIG. 6A illustrates the plots around the time when 4019 minutes (or 2019 minutes from the initiation of the plotting) elapsed. The position of the "4019 minutes" in real time is denoted by an outline arrow in the figure; however, the data of the fluorescence detector B have further progressed to the position t1, which is approximately 0.3 minutes longer than real time. This corresponds to +150 [ppm] of the frequency deviation of a crystal oscillator. On the other hand, the data of the fluorescence detector A have only progressed to the position t2, which is before the "4019 minutes" and approximately 0.08 minutes shorter than real time. This corresponds to −40 [ppm] of the frequency deviation of a crystal oscillator. The data of the cell temperature and the column oven temperature on the screen are updated, based on the monitoring information sent from a unit which is different from the detector, in correspondence to a readout request from a personal computer. Their lag against real time is as small as 0.015 minutes.

An actual chromatographic analysis does not generally require such a long time as described above. However, for example, if an analysis operator commands the initiation of an analysis before going home on Friday to perform the analysis during the night and weekend and comes to work on Monday morning to view the result, the output screen shows such a state as FIG. 6A. Since this output screen obviously shows that the apparatus internal time is not accurate, even if this does not cause substantial problems, the analysis operator doubts the accuracy of the detector, which might damage his or her credibility of it. In particular, the longer the elapsed time becomes from the initiation of an analysis, the more the difference becomes between real time and the apparatus internal time, and the aforementioned problem becomes more prominent.

Recently, the advance of the technique of chromatographic analysis has made it possible to obtain very steep peaks, requiring a higher temporal accuracy than before for the retention time of such steep peaks. Nevertheless, there is also a more practical problem in that such an inaccuracy of the apparatus internal time as described earlier makes it difficult to reduce the error of the retention time.

Patent Document 1: Japanese Unexamined Patent Application Publication No. H06-174709

SUMMARY OF THE INVENTION

The present invention has been achieved to solve the aforementioned problems, and the main objective thereof is to provide a detector for a chromatograph capable of obtaining an accurate retention time of each peak on a chromatogram by synchronizing the apparatus internal time after the repetition of data sampling with real time as much as possible, and capable of synchronizing the progress of the chromatograms by a plurality of detectors which operate simultaneously and in parallel, and synchronizing the renewal of other monitoring information and the progress of a chromatogram.

The present invention achieved to solve the aforementioned problems provides a detector for a chromatograph, for sequentially detecting sample components separated by a chromatographic analysis as time progresses, including:

a) an A/D conversion unit for sampling an analog detection signal at predetermined data sampling intervals to convert it to digital data; and b) a signal generator for counting a reference clock signal for indicating the timing of a data sampling to the A/D conversion unit, and for generating an indication signal in which a time control is performed in such a manner that N (where N is an integer equal to or more than two) consecutive data sampling intervals are defined as a time adjustment period, where each of M (where M is an integer less than N) consecutive data sampling intervals becomes longer or shorter than each of other N−M data sampling intervals by a predetermined number of counts.

The "chromatograph" in the present invention can be any apparatus, such as an LC and GC, for temporally separating the components contained in a sample. The detector for a chromatograph according to the present invention can be any apparatus that continuously obtains an analog detection signal in any manner and converts the detected signal to digital values by an A/D conversion unit, and its method and principle of the detection are not specifically limited.

In a conventional and general detector for a chromatograph, the data sampling interval always remains constant in a sampling period. On the other hand, in the detector for a chromatograph according to the present invention, the data sampling interval does not always remain constant but each of M data sampling intervals in a time adjustment period may be longer or shorter than each of the other data sampling intervals in a sampling period. Even in this case, if N, M, and the "predetermined number of counts" remain constant, the length of the time adjustment period remains constant.

For example, if N and the "predetermined number of counts" are predetermined, the length of the time adjustment period changes according to the value of M. If each of M data sampling intervals is set to be longer than each of N−M data sampling intervals by the predetermined number of counts, increasing the value of M relatively elongates the time adjustment period. In the case where the frequency deviation of a crystal oscillator used as the source of a reference clock signal is a positive value, the period of time for a given number of counts becomes shorter than in the case where the frequency deviation is zero. Thus, by increasing the value of M, the number of counts per time adjustment period is increased, elongating one time adjustment period. In this manner, the length of the time adjustment period in real time and that of the time adjustment period in the apparatus internal time based on a reference clock signal with a frequency deviation can be almost equalized.

To adjust the time as described above, the "predetermined number of counts" may be changed in place of the value of M. In this case, however, the difference of the data sampling intervals might become extremely large to cover an adequately wide range of the frequency deviation. Since this is rather undesirable, in practice, it is preferable to adjust the time lag by the value of M with the value of the "predetermined number of counts" prefixed. That is, one embodiment of the detector for a chromatograph may further include a parameter setting means for setting time adjustment parameters to the signal generator in accordance with a sampling period, the time adjustment parameters including a first parameter corresponding to the N−M data sampling intervals and a second parameter indicating the value of M.

In this embodiment, the time adjustment parameters may be so determined that the progress of time inside the detector for a chromatograph which accompanies the repetition of data sampling based on the reference clock signal corresponds to the progress of real time.

Even if a crystal oscillator has a frequency deviation, if the variation of the deviation is small, the time adjustment parameters can be experimentally determined in advance and these time adjustment parameters can be commonly applied to every detector using a crystal oscillator with a small variation of the frequency deviation. That is, it is not necessary to use different adjustment parameters for each detector. On the other hand, in the case where the frequency deviations of the detectors vary widely or the frequency deviations show significantly different dependency on the temperature or other factors, it is required to use appropriate time adjustment parameters for each detector. However, manually obtaining the appropriate time adjustment parameters for each detector is inefficient.

Given this factor, the present invention provides an adjustment method of the detector for a chromatograph, including the following steps:

a jig for clocking a standard period of time having a predetermined length is connected to the detector for a chromatograph;

the number of counts of the reference clock signal in the signal generator is obtained for the standard period of time;

the time adjustment parameters based on the number of counts is automatically computed; and the time adjustment parameters are stored in a memory unit of the parameter setting means.

In this adjustment method, only the simple operation of connecting the jig to the detector and pushing a button for ordering the start of adjustment, for example, is required to automatically set appropriate time adjustment parameters. Hence, an adjustment to eliminate the difference between the apparatus internal time and real time can be easily performed for each detector.

The detector for a chromatograph according to the present invention provides a high degree of synchronization of the apparatus internal time and real time, even in the case where the frequency deviation of a crystal oscillator for generating a reference clock signal is large. This increases the absolute precision of the retention time of each peak appearing on a chromatogram. Further, also in the case where an eluate from a column is bifurcated to be simultaneously and in parallel detected by a plurality of detectors, the progresses of the chromatograms created in real time based on the detection signals by the plurality of detectors can be synchronized, and the retention times for the same component can also be synchronized. In addition, the timing of the renewal of other monitoring information directly obtained from a column oven, for example, and the progress of a chromatogram can be synchronized. Therefore, the unnaturalness of the display on the output screen showing the chromatogram can be eliminated, increasing the user's sense of trust in the apparatus.

BRIEF DESCRIPTION OF THE DRAWINGS

FIG. 5 is a flowchart illustrating the flow of an automatic parameter-setting process.

EXPLANATION OF THE NUMERALS

1 . . . Mobile Phase Container
2 . . . Liquid Sending Pump
3 . . . Injector
4 . . . Column Oven
5 . . . Column
6 . . . Detector
   61 . . . A/D Converter
   62 . . . Drive Unit
   63 . . . Time Adjustment Controller
   64 . . . Time Adjustment Counter
8 . . . Controller
9 . . . Data Processor
10 . . . Operation Unit
11 . . . Display Unit
20 . . . Time Adjustment Value Memory
21 . . . Interval Register
22 . . . Interpolation Register
23 . . . Preset Value Generator
24 . . . Reference Clock Generator
25 . . . Down Counter
26 . . . Divide-By-256 Counter
30 . . . Time Adjustment Jig
31 . . . 60-Minute Timer

DETAILED DESCRIPTION OF PREFERRED EMBODIMENTS

Figure 1:
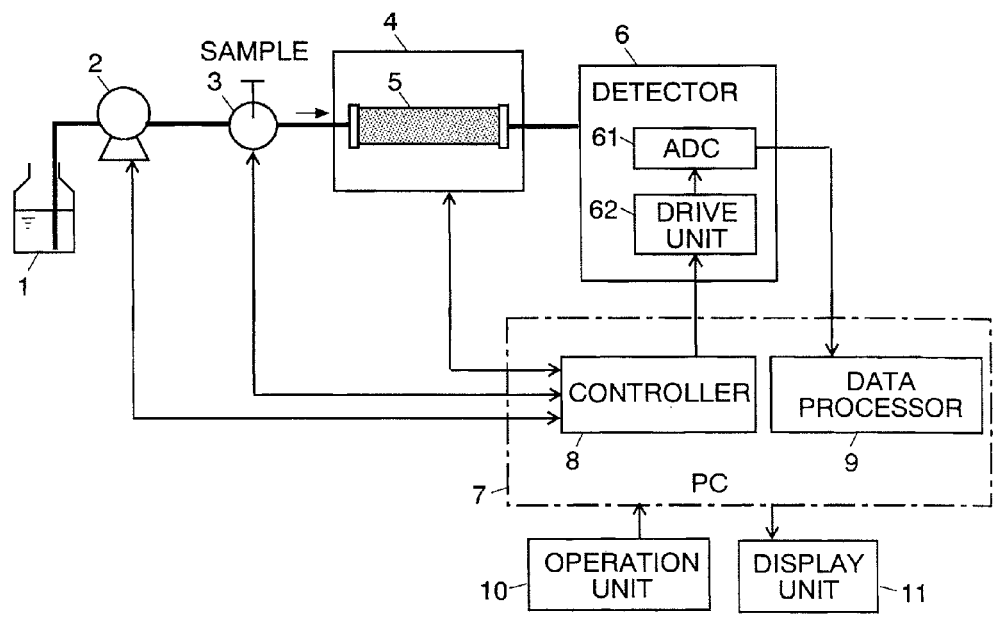
FIG. 1 is a schematic configuration diagram of an LC system using the detector for a chromatograph according to the present invention.

An embodiment of the liquid chromatograph (LC) system using the detector for a chromatograph according to the present invention will be described with reference to the attached figures. FIG. 1 is an entire schematic configuration diagram of the LC system according to the present embodiment.

In FIG. 1, the sending pump 2 sucks a mobile phase from the mobile phase container to send it to the column 5 through the injector 3 at an approximately constant flow rate. The injector 3 injects a sample liquid to the mobile phase at a predetermined time point, in correspondence to the control signal supplied from the controller 8. The sample liquid is sent to the column 5 by the flow of the mobile phase, and a variety of components in the liquid sample are temporally separated while passing through the column 5. The column 5 is contained in the column oven 4, and its temperature is controlled at a constant temperature or in accordance with a predetermined heating program under the control of the controller 8. The eluate from the column 5 is introduced to the detector 6, which sequentially detects the components contained in the eluate to generate a detection signal corresponding to their concentration.

The detector 6 includes an A/D converter (or ADC) 61 and a drive unit 62 for driving the A/D converter 61. The A/D converter 61 samples the detection signal, which is an analog signal, with a predetermined sampling period, and converts the sampled analog values into digital values to be provided to the data processor 9 as detection data. The detector 6 can be any type of detector, such as a fluorescence detector, ultraviolet/visible absorption detector, photodiode array detector, differential refractive index detector, or electric conductance detector. That is, the manner of detecting the components in an eluate is not specifically limited in this invention.

The controller 8 controls the operation of the sending pump 2, the injector 3, the column oven 4, the detector 6, and other units. The data processor 6 receives the detection signal from the detector 6 and buffers it to perform a predetermined data processing. The controller 8 and the data processor 9 achieve their functions by executing dedicated control/process software which is previously installed in the personal computer (PC) 7 with an operation unit 10 and a display unit 11. Of course, a portion of the functions can be realized by dedicated hardware.

Figure 2:
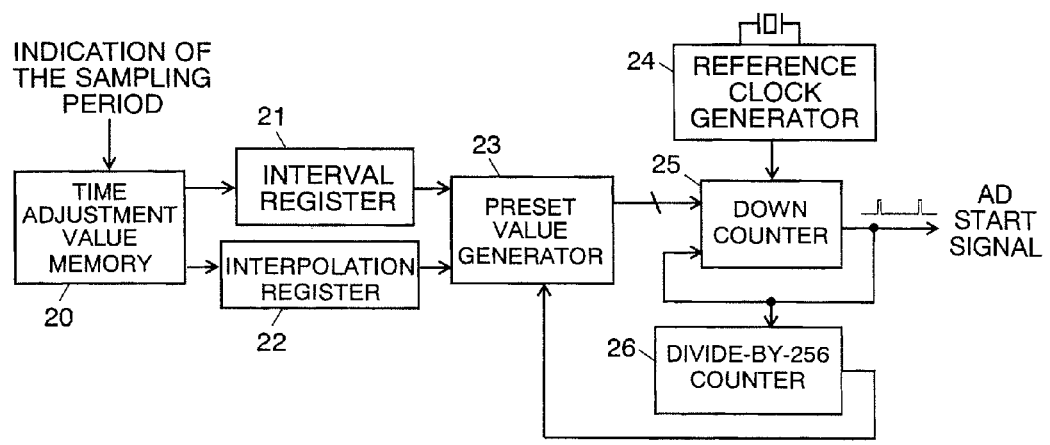
FIG. 2 is a function block diagram of the main portion of the drive unit in FIG. 1.

In the LC system of the present embodiment, the drive unit 62 included in the detector 6 has a characteristic configuration to perform a characteristic operation. FIG. 2 is a function block diagram of the main portion of the drive unit 62, which includes a time adjustment value memory 20, an interval register 21, an interpolation register 22, a preset value generator 23, a reference clock generator 24, a down counter 25, a divide-by-256 counter 26, and other units, as function blocks.

The reference clock generator 24 includes a crystal oscillator, and generates a reference clock signal with a predetermined frequency to provide it to the down counter 25. In this embodiment, it is assumed that the nominal frequency of the reference clock signal is 1 MHz (exactly speaking, there is a frequency drift corresponding to the frequency deviation of the crystal oscillator). The down counter 25 starts counting down from a preset value every time the reference clock signal is supplied, and provides a pulse signal when the count value becomes zero. With this pulse signal, the down counter 25 loads the preset value again and the divide-by-256 counter 26 counts up. This pulse signal also serves as an AD start signal, which is a signal for indicating the timing of performing the data sampling in the A/D converter 61. The interval between two temporally adjacent AD start signals is the data sampling interval.

The preset value generator 23 receives the following input values: an interval value stored in the interval register 21, an interpolation value stored in the interpolation register 22, and the output (any value between 0 and 255) of the divide-by-256 counter 26, and provides a preset value determined by the interval value and the interpolation value in correspondence to the output value of the divide-by-256 counter 26. In the time adjustment value memory 20, the interval values and interpolation values corresponding to a plurality of sampling periods (e.g. 20 [msec] and 5 [msec]) are previously memorized, and the time adjustment value memory 20 provides an appropriate interval value and interpolation value in correspondence to the indication of the sampling interval from the controller 8 to set them to the interval register 21 and the interpolation register 22 respectively.

The drive unit 62 illustrated in FIG. 2 may be configured by combining discrete logic ICs; alternatively, the same function can also be realized, for example, by writing a predetermined program to a complex programmable logic device (CPLD).

Figure 3:
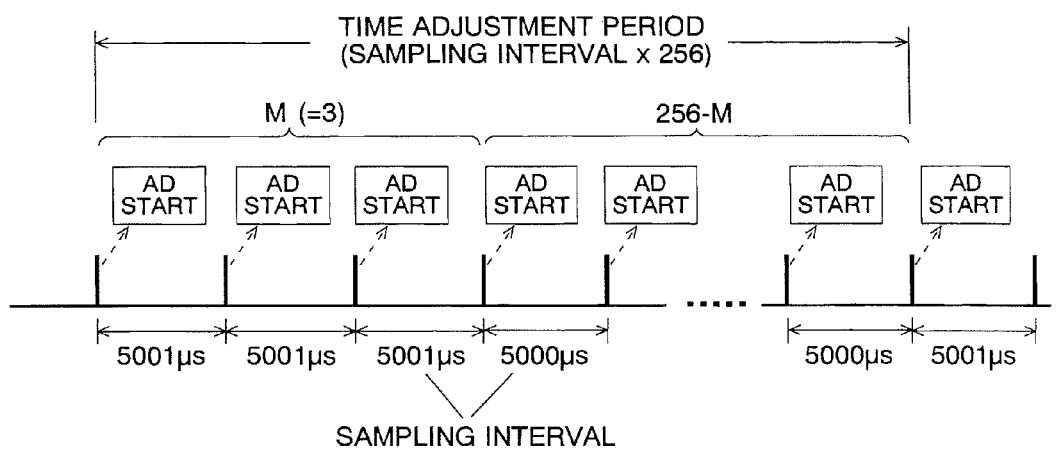
FIG. 3 is a time chart illustrating an example of the operation of the drive unit of FIG. 2.

FIG. 3 is a time chart illustrating an example of the operation of the drive unit 62. An example of the operation of the drive unit 62 will be described with reference to FIGS. 2 and 3.

As an example, it is assumed that the interval value=5000 and interpolation value=3 are memorized in correspondence to the sampling period of 5 [msec] in the time adjustment value memory 20. When the indication that the sampling period is 5 [msec] is provided to the drive unit 62 from the controller 8, the interval value and the interpolation value are read out from the time adjustment value memory 20, and they are set to the interval register 21 and the interpolation register 22 respectively. In this example, the period in which the output of the divide-by-256 counter 26 changes from zero to 255 is considered to be one time adjustment period. That is, N=256 and the interpolation value is M. The preset value generator 23 sets the interval value as the basic preset value, and sets a value in which "1" is added to the interval value as the preset value for the data sampling intervals from the start point of the time adjustment period. The number of these data sampling intervals is given by the interpolation value. Therefore, in the case where the interval value is 5000 and the interpolation number (M) is 3, the preset value for three data sampling intervals from the initiation of the time adjustment period is 5001, and that of the remaining N−M=253 data sampling intervals is 5000.

The preset values are loaded into the down counter 25 and counted down by the reference clock signal whose period is 1 [μsec] on the basis of the apparatus internal time. If the preset value is 5000, the interval of the AD start signal (or data sampling interval) becomes 5 [msec] on the basis of the apparatus internal time, and if the preset value is 5001, the interval of the AD start signal becomes 5.001 [msec] on the basis of the apparatus internal time. That is, as illustrated in FIG. 3, each of the first three data sampling intervals in one time adjustment period is 5.001 [msec] on the basis of the apparatus internal time, and each of the remaining 253 data sampling intervals is 5 [msec] on the basis of the apparatus internal time. Accordingly, one time adjustment period is 1280.003 [msec] on the basis of the apparatus internal time, which will be repeated. When averaged, this is equivalent to the situation where the data sampling interval has been 5000+(3/256)=5000.01172 [μsec].

When the sampling period is 5 [msec], the data sampling interval in real time should be 5.000 [msec], whose difference from the 5.00001172 [msec] on the basis of the apparatus internal time as previously described corresponds to +2.3 [ppm]. In other words, by setting the interval value to be 5000 and the interpolation time to be 3 in the case where the frequency deviation of the crystal oscillator of the reference clock generator 24 is +2.3 [ppm], the average data sampling interval becomes 5 [msec] in real time; hence, the time gap between the apparatus internal time and real time becomes substantially zero and the apparatus internal time becomes identical to real time.

When the interpolation value M is 1 and the frequency deviation of the crystal oscillator is +0.78 [ppm], the time gap between the apparatus internal time and real time becomes almost zero, and this is the smallest resolution of the time adjustment. Since the interpolation value M can be set to be any value between 0 and 255, the time lag can be adjusted for the frequency deviation up to the maximum of 199 [ppm]. If the interval value is set to be "4999" and the interpolation value M is set between 0 and 255, a negative frequency deviation can also be adjusted. Furthermore, since the interval value can be set to be equal to or less than "4998" or equal to or more than "5001," the drive unit 62 having the aforementioned configuration can adjust the frequency deviation, in the case where the sampling period is 5 [msec], with the resolution of 0.78 [ppm] without the limitation of the range of frequency. When the analysis time is 3600 minutes which correspond to 2.5 days of a weekend, 0.78 [ppm] corresponds to approximately 0.003 minutes=0.2 seconds. That is, even after 2.5 days from the initiation of the analysis, the lag between the progress of the chromatogram and real time is only 0.2 seconds, which is practically negligible.

In the aforementioned time adjustment operation, there are two data sampling intervals of 5 [msec] and 5.001 [msec] on the basis of the apparatus internal time; however, in broad terms, such a difference can be negligible.

The examples of the aforementioned values were for the case of the sampling period of 5 [msec]. When the sampling period is 20 [msec] for example, it is evident that both the interval value and the resolution of the time adjustment become different.

Since the driving unit 62 performs a time adjustment operation as previously described, by appropriately setting the interval value and the interpolation value, the lag between the apparatus internal time and real time can be reduced to substantially zero. The frequency deviation of a crystal oscillator is mostly attributable to the intrinsic prime deviation that the oscillator has, and also slightly to some deviations depending on the variability of the capacitor for oscillation and on the environmental conditions such as temperature and humidity. On the other hand, the temporal variation of deviation by the use of the crystal oscillator is negligible. Since generally the as-manufactured prime frequency deviations of the crystal oscillators in the same production lot can be considered to be equal, the appropriate interval value and interpolation value for a predetermined sampling period can be previously set, and little correction by the user is required. Accordingly, it is generally possible for the manufacturer of the detector to check the frequency deviation of the reference clock signal of a plurality of detectors under the standard environment, and based on the result, determine the interval value and the interpolation value with which the lag between the apparatus internal time and real time becomes smallest.

Figure 4:
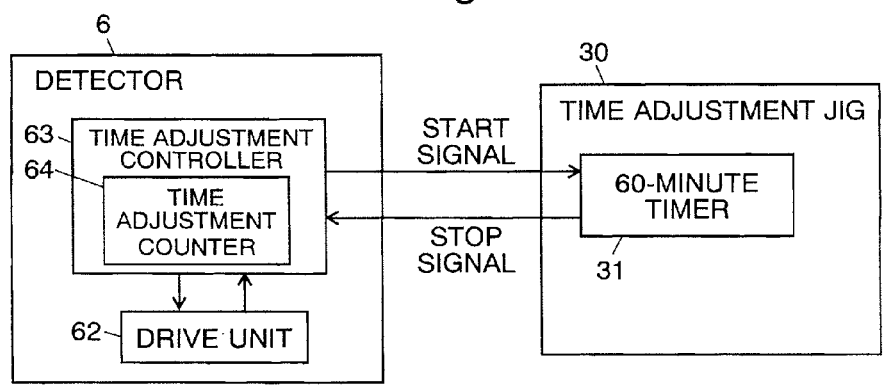
FIG. 4 is a schematic configuration diagram for explaining an automatic setting of the time adjustment parameters.

In the case where the individual differences of the frequency deviations of crystal oscillators are also taken into consideration, it is preferable that the optimum interval value and the interpolation value be determined for each detector to be stored in the time adjustment value memory 20. An example of automatically setting the parameters for determining the optimum interval value and the interpolation value for each detector will now be described. To perform this automatic setting, a time adjustment jig 30 as illustrated in FIG. 4 is used. The time adjustment jig 30 includes a 60-minute timer with very high time accuracy, which begins clocking upon receiving a start signal from outside and provides a stop signal when 60 minutes have elapsed. The detector 6 has a time adjustment controller 63 which corresponds to the interface between the previously described drive 62 and the time adjustment jig 30. The time adjustment controller 63 includes a time adjustment counter 64 for counting the AD start signal.

FIG. 5 is a flowchart illustrating the flow of an automatic parameter-setting process. In this example, the parameters for the sampling interval of 5 [msec] are to be set. First, the time adjustment controller 63 sets "5000" to the interval register 21 of the drive unit 62 and "0" to the interpolation register 22 (Step S10). Accordingly, the preset value generated in the preset value generator 23 is always "5000." Next, the preset value is loaded to the down counter 25, the time adjustment counter 64 is reset to zero, and the start signal is sent to the time adjustment jig 30 (Step S11). Consequently, the down counter 25 starts counting down from the preset value "5000," and the time adjustment counter 64 and the 60-minute timer 31 simultaneously start counting. The time adjustment counter 64 counts up every time the AD start signal is provided (Step S12).

Next, the time adjustment controller 63 determines whether or not the stop signal is provided from the time adjustment jig 30 (Step S13). If NO, the process returns to Step S12. The stop signal is not provided until the 60-minute timer 31 reaches precisely 60 minutes as previously described, and the time adjustment counter 64 continues to count the AD start signal until then. When exactly 60 minutes have elapsed since the start signal is provided to the time adjustment jig 30 and the stop signal is provided to the time adjustment controller 63, the process proceeds from Step S13 to Step S14, in which the time adjustment controller 63 stops the count of the time adjustment counter 64 and obtains the count value C then. Next, in Step S15, the data sampling interval T [μsec] on the basis of the apparatus internal time is computed by the following equation (1):

$$T=5000\times(\text{count value } C/720000) \qquad (1).$$

This "720000" is the count value for 60 minutes in the case where the data sampling interval is exactly (i.e. on the basis of real time) 5 [msec].

After that, both the integer portion of T obtained by the equation (1) and [the decimal portion of T]×256 are computed, and the former is determined to be the interval value, and the latter the interpolation value (Step S16). Assuming that, for example, the frequency deviation of the crystal oscillator of the reference clock generator 24 is +150 [ppm], the count value C will be increased by the frequency deviation to be 720108. Substituting this count value C into the expression (1) gives T=5000.75. Therefore, in Step S16, the interval value is obtained to be 5000. Meanwhile, the interpolation value is obtained to be 0.75×256=192. The interval value and interpolation value obtained in this manner are related to the sampling period to be memorized in the time adjustment value memory 20 (Step S17). If there are plural sampling periods, the initial value of the interval value in Step S10 may be changed for every sampling period, the equation (1) may be accordingly modified, and the same process as in the flowchart may be repeated.

Figure 6A:
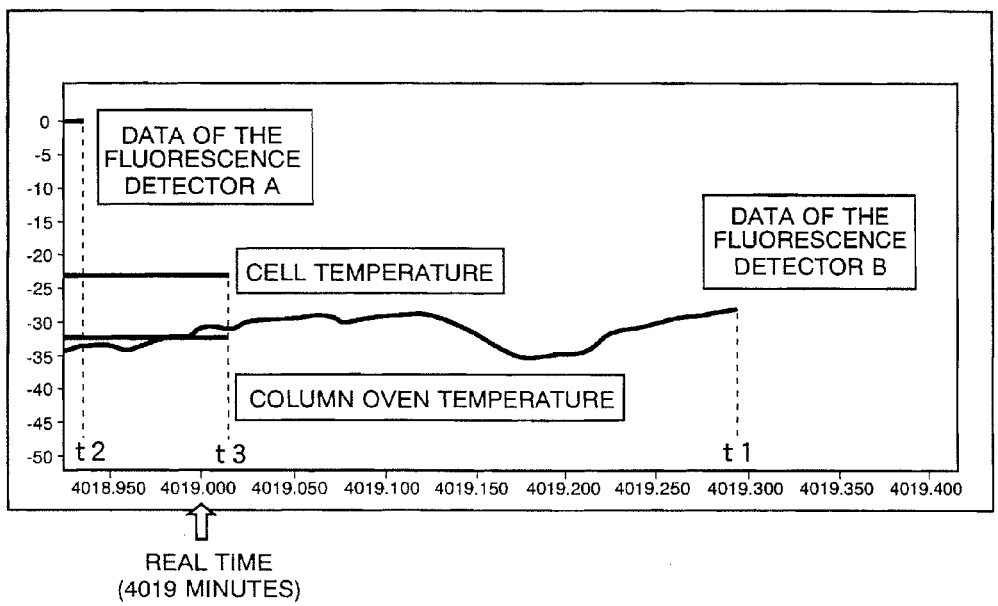
FIG. 6 illustrates an example of the output screen displayed after a predetermined time has passed from the initiation of an analysis in a conventional LC system and the LC system according to the present embodiment.
Figure 6B:
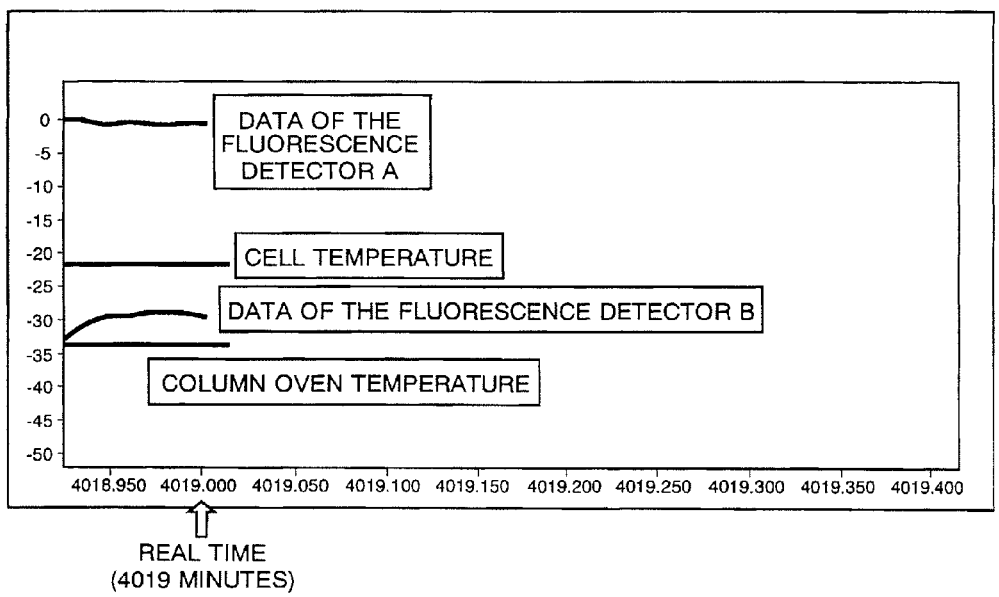

The automatic parameter setting using the time adjustment jig 30 as previously described enables an easy setting of the interval value and interpolation value for each detector, almost eliminating the gap between the apparatus internal time and real time in each detector. Consequently, the output screen under the same conditions of FIG. 6A will be as illustrated in FIG. 6B. That is, the progress of the detection data (or chromatogram data) by a plurality of detectors for detecting the same eluate in parallel is almost conformed to that of real time, eliminating the unnaturalness of the display as illustrated in FIG. 6A and increasing the accuracy of the retention time of peaks on the chromatogram.

It should be noted that the embodiment described thus far is merely an example of the present invention, and it is evident that any modification, adjustment, or addition made within the sprit of the present invention will be included in the scope of the claims of the present application.

For example, the configuration of the drive unit 62 as previously described is merely an example, and a person skilled in the art would easily arrive at a configuration that can realize the equal function. The value of N, and the count value ("1" in the aforementioned example) to be added in the data sampling intervals whose number is specified by the interpolation value M may be appropriately changed. A predetermined count value may be subtracted in the data sampling intervals specified by the interpolation value M. The data sampling intervals in which the count value is added or subtracted may be positioned at any timing in a time adjustment period.

The detector in the aforementioned embodiment is applied to an LC system. It is evident that the detector can be applied to other chromatographic analysis systems such as a gas chromatograph.

What is claimed is:

1. A method, for sequentially detecting sample components separated by a chromatographic analysis as time progresses, comprising:
   a) sampling an analog detection signal at predetermined data sampling intervals to convert it to digital data;
   b) counting a reference clock signal for indicating a timing of a data sampling to an A/D converter and generating an indication signal in which a time control is performed in such a manner that N (where N is an integer equal to or more than two) consecutive data sampling intervals are defined as a time adjustment period, where each of M (where M is an integer less than N) consecutive data sampling intervals becomes longer or shorter than each of other N−M data sampling intervals by a predetermined number of counts; and
   setting time adjustment parameters in accordance with a sampling period, the time adjustment parameters including a first parameter corresponding to the N−M data sampling intervals and a second parameter indicating the value of M.

2. The method according to claim 1, wherein the time adjustment parameters are so determined that a progress of time inside a detector for a chromatograph which accompanies a repetition of data sampling based on the reference clock signal corresponds to a progress of real time.

3. The method according to claim 1 further comprising the following steps before the sampling step:
   connecting a detector for a chromatograph to a jig for clocking a standard period of time having a predetermined length;
   obtaining a number of counts of the reference clock signal in the signal generator for the standard period of time;
   automatically computing the time adjustment parameters based on the number of counts; and
   storing the time adjustment parameters in a memory unit of the parameter setting means.

4. The method according to claim 2 further comprising the following steps before the sampling step:
   connecting a detector for a chromatograph to a jig for clocking a standard period of time having a predetermined length;
   obtaining a number of counts of the reference clock signal in the signal generator for the standard period of time;
   automatically computing the time adjustment parameters based on the number of counts; and
   storing the time adjustment parameters in a memory unit of the parameter setting means.

* * * * *